United States Patent [19]

Dinka

[11] 4,189,535

[45] Feb. 19, 1980

[54] SERUM CELL GROWTH PROMOTING MATERIALS

[75] Inventor: Stephen K. Dinka, Washington Crossing, Pa.

[73] Assignee: The United States of America as represented by the Secretary of Agriculture, Washington, D.C.

[21] Appl. No.: 935,217

[22] Filed: Aug. 21, 1978

[51] Int. Cl.² ............................................. A01N 1/02
[52] U.S. Cl. ........................................................ 435/2
[58] Field of Search ........................................ 195/1.8

[56] References Cited

PUBLICATIONS

Paul et al., Proc. Nat. Acad. Sci., vol. 68, No. 3, (Mar. 1971) pp. 645–648.
Pierson et al., J. Cell Physiol., vol. 79 (1972), pp. 319–330.
Lieberman et al., J. of Biol. Chem., vol. 233 (1958), pp. 637–642.
Antoniades et al., Proc. Nat. Acad. Sci., vol. 72, No. 7 (Jul. 1975), pp. 2635–2639.

*Primary Examiner*—Sam Rosen
*Attorney, Agent, or Firm*—M. Howard Silverstein; W. E. Scott; David G. McConnell

[57] ABSTRACT

A composition comprising material suitable for promoting cell growth and its preparation from serum is described.

11 Claims, No Drawings

SERUM CELL GROWTH PROMOTING MATERIALS

TECHNICAL FIELD

This invention relates to serum growth materials, particularly to compositions of such materials and methods for their preparation.

BACKGROUND OF THE INVENTION

In order to understand cell growth of both normal and abnormal cells, scientists have sought to grow cells in chemically defined culture media. Nearly all animal cells in culture require serum for growth and serum is added to nutrient media. However, serum is a complex material containing many substances. The non-nutrient entities present in serum which promote cell growth have been termed "growth factors." Some growth factors have specific tissues as their target while others cause growth of broader spectrum of cell types. Numerous scientists have sought means to isolate and purify factors responsible for cell growth. Although some factors are chemically identifiable as steroid or polyamine in nature, most of the substances are polypeptide or protein in nature. Isolation and purification of these low concentrations of proteins in complex systems by present techniques are extremely difficult.

A technique employed and reported frequently in the prior art is protein fractionation employing various precipitating agents such as ethanol (R. S. Chang et al., Proc. Soc. Exptl. Biol. & Med., 102(1):213–217 (1959); H. Katsuta et al., Jpn. J. Exp. Med., 29:297–309 (1959)), zinc (R. S. Chang et al., loc. cit.) and ammonium sulfate (J. Michl, Exp. Cell. Res. 23:324–334 (1961); H. Katsuta et al, loc. cit.). This technique is cumbersome, usually involving many steps and not infrequently causing denaturation of some of the protein. A sequential combination of different techniques has also been employed. Thus, for example, R. W. Pierson, Jr. et al., J. Cell. Physiol., 79:319–330 (1972), reported a three technique procedure: chromatography, gel-filtration and polyacrylamide gel electrophoresis; R. Hoffman et al., Exp. Cell. Res. 85, 275–280 (1973), described a multi-technique procedure which include the techniques of ammonium sulfate precipitation, differential flotation, chromatographic separation, gel filtration, immunodiffusion and electrophoresis; and I. Lieberman et al., J. Biol. Chem., 233 (3):637–642 (1958) described a multitechnique procedure which include ammonium sulfate precipitation, twofold ethanol precipitation and chromatography on diethylaminoethylcellulose. Each technique of the multi-technique procedure generally requires several steps rendering these methods cumbersome. A substantially single technique separation, namely, paper curtain electrophoresis was employed by R. Holmes et al., J. Biophys. Biochem. Cytol. 10:389–401 (1961); however, this method is not very suitable for large scale preparation. Also H. Katsuta et al., loc. cit. used zone electrophoresis for separation but this method is less adaptable for large scale preparation. Although H. N. Antoniades et al., Endocrinology: 70:95–98 (1962) have reported an isolation of insulin-like complex (different material) from serum using chromatographic technique with a cation exchange resin, when that technique was used subsequently by Pierson et al., loc cit, for growth factor isolation, the isolated material retained only a minor part of the activity. This is illustrative of the problems encountered for as pointed out in the review article by D. Gospodarowicz et al., Ann. Rev. Bioch. 45, 531–558 (1976) during isolation, growth factors with additive or synergistic effect may be separated resulting in fractions that are much less active individually. A further difficulty pointed out is that the mitogen might account for only from $5 \times 10^{-6}$ to $2 \times 10^{-2}$ percent of the protein in the serum.

It is seen that the heretofore published methods are cumbersome, requiring a combination of techniques, or are not economically feasible or adaptable to a moderate or large scale operation, or do not provide a method for isolating the growth material without inactivation. It is desirable to have a simpler method for obtaining serum growth factors freed of many of the non-growth promoting substances. It is further desirable for any cell culture work to have a purified growth factors preparation instead of whole serum with its complex and varying composition.

In addition, there are not only many areas of practical application in which there may be made beneficial substitution of purified serum growth materials for whole serum, but the availability of growth material would make possible new areas of application of cell growth regulation. Some of the areas in which the availability of purified serum growth materials would be highly advantageous include in the study and cure of neoplastic diseases, dwarfism, and mental development (nerve growth factor), in the study of cellular immunity, in replacing serum for virus vaccine production, and for biomolecules production (e.g. urokinase or interferon production), in tissue grafting in burn cases, in animal husbandry for increasing and maintaining rapid growth, and wherever serum is required for tissue growth. Thus, it is seen that a purified growth material preparation is desirable for many applications.

DESCRIPTION OF THE INVENTION

According to the present invention there has been discovered a process for obtaining purified growth promoting material from serum which is simple and economically feasible, and further there has been obtained a purified growth promoting preparation having qualities not obtained in the literature described processes. The novel composition comprising growth promoting material may be prepared from serum employing a single technique, namely, chromatography in a simple, substantially two-step operation: specific adsorption and elution.

The "growth promoting material" of the present invention may be one or more growth factors, i.e., chemical entities promoting cell mitosis. It may be a combination of materials which act together to promote cell growth. The growth promoting material has been found to be useful for promoting the growth of various cells, such as epithelial cells, fibroblasts, primary cells (e.g. bovine kidney cells), and the like, and it appears to have broad growth promoting activity. Moreover, it has been found that the growth promoting material of the present invention may be obtained from serum without significant loss in activity.

The growth promoting material may be prepared by (1) contacting serum at a pH in the range of 8 to 11 with an anion exchanger to adsorb growth promoting material thereon, and (2) eluting said growth promoting material from the exchanger with gradient salt solutions or gradient pH solutions preferably, in a physiological buffer system.

The serum employed in the first step of the reaction may be obtained in a conventional manner from blood, usually mammalian blood. Conveniently, particularly for ultimate production on a large scale, bovine serum which is obtainable commercially may be employed. Alternatively, serum may be obtained from collected blood, particularly mammalian blood by centrifuging and filtering. Sources of mammalian blood include bovine, ovine, porcine, human canine, feline blood and others. Bovine blood is preferred. Serum may be stored, preferably in the frozen state, prior to use.

It is important for the success of this process and the recovery of the desired product that the pH of serum be adjusted to that within the above identified range. A more preferred range is 9.5 to 10.5. Sodium hydroxide solution generally is preferred for making this adjustment.

The anion exchanger or anion exchange material to be employed is preferably carbohydrate based, i.e., one with a carbohydrate backbone such as commercially available dextran, cellulose and agarose exchangers. The group on the exchanger may be a tertiary amine, a quaternary ammonium group or other suitable groups. Some commercial anion exchangers with polystyrene backbone have not been found to be suitable for the preparation of the growth promoting materials of the present invention.

In carrying out the first step of the reaction, the pH of the serum is adjusted to the above indicated range by adding preferably a sodium hydroxide solution while the temperature is maintained in the range of from about 1° to 6° C. To the alkaline serum is added an appropriate anion exchanger and the mixture stirred for about 16 to 24 hours while the temperature is maintained below about 5° C. to adsorb growth promoting material on the exchanger.

The anion exchanger bearing the growth promoting material may be mechanically separated from the alkaline serum by filtering, centrifuging or simply placing the exchanger suspension in a column suitable for the elution step and allowing the serum to drain. The exchanger then is prepared for the elution step by washing with a physiological buffer system, preferably sodium phosphate buffer of 0.05 M or lower at a pH in the range 7.0 to 7.6 until the wash solution shows a low and substantially constant optical density at 280 m$\mu$, the wavelength widely used to estimate protein concentration. For washing, it has been found desirable to avoid inclusion of sodium chloride in the washing solution since its presence tends to cause leaching of the growth promoting material from the exchanger.

The elution step may be carried out in a batch or continuous process. When employing a batch process, the washed exchanger is admixed in successive steps with appropriate volumes of eluting agent of appropriate concentrations to provide a suitable gradient and the growth promoting material recovered in the eluate. When employing a continuous process, a column is employed. In this procedure, the washed exchanger bearing growth promoting material is placed in the column and eluting agents of appropriate concentrations to provide a suitable gradient may be successively placed in the head reservoir at appropriate intervals or placed in reservoirs of an automatic continuous gradient forming apparatus, and the eluting agent allowed to flow down the column to elute the growth promoting material which then is recovered in the eluate.

Suitable columns for a continuous process are those of inert materials. The preferred material for the columns is glass.

The elution is carried out preferably employing physiological solutions. The preferred eluant is sodium chloride in a phosphate buffer system at a pH in the range 7.0 to 7.6, preferably 7.2. The concentration range of the sodium chloride solutions is from about 0.05 M to about 2.0 M. The desired growth promoting material is recovered in the eluate primarily in the fractions eluted with chloride ion concentration above 0.1 M, preferably in the range of from about 0.15 M to about 1.6 M. The eluate thus obtained containing the growth promoting material may be employed immediately or stored at low temperatures for future use. For application, the eluate is adjusted to physiological conditions, e.g. ionic strength and pH. Known procedures such as dialysis against physiological buffer systems or other desalting procedures may be employed in accomplishing this. The material is then sterile filtered using known procedures.

A preferred process for producing a composition comprising material suitable for promoting cell growth comprises (1) adding sodium hydroxide solution to serum at temperatures maintained in the range of 1° to 6° C. and mixing until the pH of the serum is in the range of about 9.5 to 10.5, (2) adding to the resulting alkaline serum, a carbohydrate backboned anion exchanger and mixing for a period of from about 16 to 24 hours while the temperature is maintained below about 5° C. to adsorb growth promoting material on the anion exchanger, (3) mechanically separating the resulting exchanger from the liquid, (4) washing the exchanger with 0.05 M sodium phosphate buffer solution of pH 7.2 until the wash solution shows a substantially constant optical density at 280 m$\mu$, (5) eluting the gradient sodium chloride solution in the concentration range of about 0.2 M to about 2.0 M, said sodium chloride solution being preferably in a phosphate buffer, and (6) recovering the eluate.

The elution may be carried out employing pH gradient solutions, preferably physiological buffered solutions. In such operations, solutions of successively decreasing pH from a pH of about 10.5 to about 4 are employed in a manner similar to that described for salt solutions and the eluates recovered also in like manner. In this method, chemically different buffer systems are necessary to provide the appropriate range; it is therefore less preferred to elution employing a salt gradient solution.

The compositions comprising growth promoting materials prepared as described above and freed of extraneous materials retain the essential growth promoting activity of unmodified serum and are adapted to be employed in promoting growth of various cells.

Demonstrations of effectiveness of the compositions in promoting cell growth may be shown by the hereinafter described cell culture experiments in which the new and control compositions are added to cell suspensions in nutrient culture medium and determining the effect on growth. Representative test cell systems include feline tongue cells, canine kidney cells and bovine kidney cells. Representative nutrient culture medium suitable for carrying out the tests are those referred to as Eagle's minimum essential medium (originally described by Eagle, H. in Science, 130:432 (1959)) or modified with Earle's salts (Natl. Cancer Inst., 4:167 (1943)) and available commercially (e.g. Grand Island Biological Company, Grand Island, N.Y. or K.C. Biological, Inc., Lexena, Kansas). Commercially obtained Eagle's medium modified with Earle's salts to which had been added non-essential amino acids, sodium pyruvate and the antibiotics penecillin G, streptomycin sulfate and amphotericin B, were employed as the basic nutrient culture medium in the hereinafter described representative experiments.

In the tests, there are separately added to appropriate cell suspensions in nutrient medium serum control, non-dialyzed serum after adsorption and dialyzed sterile eluate diluted with medium in amounts to provide varying concentrations of test and control samples for determining cell growth. The samples are prepared in duplicate and placed in culture trays and incubated at 37° C. in a carbon dioxide incubator (5 percent carbon dioxide) for two days or longer. Eluates containing the growth promoting material of the present invention are found to promote growth of normal looking cells and to retain the activity present in the original serum.

The novel growth promoting material produced by the process of the present invention has additional advantages in being resistant to degradation frequently cause by lyophilization or $\gamma$-irradiation. This is of great practical value since it facilitates shipping or storage without significant loss of growth promoting activity and can eliminate undesirable $\gamma$ irradiation sensitive microorganisms, including viruses.

The following examples illustrate the invention but are not to be construed as limiting:

EXAMPLE I

To 1.0 liter of commercial fetal calf serum (of pH 7.3 and which had been stored at $-75°$ C.) was added at about 4° C., 3 milliliters of 10 N NaOH to adjust the pH of the serum to 10.5. Fifty milliliters of the pH adjusted serum was set aside as "serum control." To the remaining alkaline serum still at about 4° C. was added with stirring 9.5 grams of a dextran based quaternary ammonium exchanger (QAE-Sephadex A-50, product of Pharmacia Co., Upsala, Sweden) and the stirring continued for about 19 hours while the low temperature was maintained to adsorb growth material thereon. At the end of this period the anion exchanger gel suspension was filtered through a 100 mesh screen to recover the exchanger. The exchanger was washed by suspending in 250 milliliters of 0.05 N sodium phosphate buffer at pH 7.2 and filtered. The process was repeated for a total of five washings.

After completion of the washings, the growth material bearing exchanger was suspended in 250 milliliters of 0.05 M sodium phosphate buffer with a sodium chloride concentration of 0.1 M and at a pH of 7.2, and thereafter filtered to elute a portion of the adsorbed material into the filtrate. The process was repeated. The filtrates of the two operations were designated Eluates 1 and 2. The process was repeated employing the same volume of solution containing sodium chloride in the same buffer system at pH 7.2 but with varying concentration of chloride as follows: twice with 0.2 M NaCl and twice with 0.5 M NaCl (Eluates 3–6). The anion exchanger then was suspended in the same volume (250 ml.) of 1 M NaCl in the same buffer system and allowed to stand overnight at 4° C. It was filtered and again suspended in the same strength solution (Eluates 7–8). This was followed by treatments with two 250 milliliter portions of 2 M NaCl phosphate buffered solutions (Eluates 9–10). The eluates were generally yellow and substantially clear except the last three which were colorless.

All the eluates were dialyzed against two 10-liter portions of physiological phosphate buffer at 4° C. with constant stirring for 21 hours. Thereafter, the samples were centrifuged, the pH of the serum control was adjusted to physiological, and all separately filtered through a sterile filtration membrane (0.45 or 0.20 micron pore size).

Effectiveness in promoting cell growth was determined by mixing thoroughly 1 milliliter samples of dialyzed eluate with 9 milliliters of bovine kidney cell suspension in nutrient medium containing about 130,000 cells per milliliter. (The cells were subcultured from commercially obtained Madin Darby bovine kidney (MDBK) cell line, registered in Registry of Animal Cell Lines, American Type Culture Collection, Rockville, Md. The nutrient medium employed was commercial Eagle's medium with Earle's salts and with the components previously enumerated.) Four milliliter samples were seeded into wells of multi-dish culture trays and incubated at 37° C. at 5 percent carbon dioxide and 100 percent humidity atmosphere for four days.

Observations of the culture dishes after this period show the elution carried out at a salt concentration of at least 0.5 M NaCl produces recovery of growth material without loss of activity present in serum (serum control) as seen in Table I.

TABLE I

| Culture Sample | Eluant | Observation |
| --- | --- | --- |
| Serum Control | — | $\approx$90% confluent, smooth cells |
| Serum After Adsorption | — | $<<$25% confluent |
| Wash 1 | — | $\leq$25% confluent, abnormal cells |
| Wash 2 | — | Attached debris, few abnormal cells |
| Wash 3 | — | Attached debris, few abnormal cells |
| Wash 4 | — | Attached debris, few abnormal cells |
| Wash 5 | — | Attached debris, few abnormal cells |
| Eluate 1 | 0.1 M NaCl | Many attached, small clumped cells, very little outgrowth |
| Eluate 2 | 0.1 M NaCl | Many attached, small clumped cells, very little outgrowth |
| Eluate 3 | 0.2 M NaCl | Many attached, small clumped cells, very little outgrowth |
| Eluate 4 | 0.2 M NaCl | Many attached, small clumped cells, very little outgrowth |
| Eluate 5 | 0.5 M NaCl | <100% confluent, smooth cells |
| Eluate 6 | 0.5 M NaCl | $\approx$90% confluent, smooth cells |

TABLE I-continued

| Culture Sample | Eluant | Observation |
|---|---|---|
| Eluate 7 | 1.0 M NaCl | ≈75% confluent, smooth cells |
| Eluate 8 | 1.0 M NaCl | ≈50% confluent, smooth cells |
| Eluate 9 | 2.0 M NaCl | <50% confluent, smooth cells |
| Eluate 10 | 2.0 M NaCl | ≈25% confluent, smooth cells |

EXAMPLE II

To 1625 milliliters of pooled adult bovine serum (pH 8.15) was added 5.4 milliliters of 10 N sodium hydroxide solution to provide a serum pH of 10.0. To 1600 milliliters of the resulting serum was added with stirring, a dextran based anion exchanger (QAE-Sephadex A-50), and the resulting mixture stirred for about twenty-four hours at about 4° C. At the end of this period the resulting swollen anion exchanger suspension at 4° C. was poured into an appropriate column (5 centimeters × 100 centimeters) and allowed to settle and drain. The suspension was washed with a 0.05 M sodium phosphate buffer of pH 7.2 containing 0.05 M sodium chloride and the washing repeated until the optical density became substantially constant at 280 m$\mu$. The washings were saved for subsequent testing of activity. The column was allowed to run dry and then wetted with the buffer-sodium chloride mixture. The adsorbed material was then eluted with buffered sodium chloride gradient solution at a flow rate of 125 milliliter per hour. The gradient solution was obtained by adding (a) to the column mixing bottle, 1 liter of a solution which is 0.05 M sodium phosphate buffer and 0.05 M sodium chloride at pH 7.2, and (b) to the reservoir bottle, 3 liters of a solution of 0.05 M sodium phosphate buffer and 2.05 M sodium chloride, the bottles being so arranged that the solution from the reservoir bottle continuously drains into the mixing bottle at the rate of elution. After 200 tubes of samples of about 3750 milliliters were collected, the collection was terminated. The samples entering the collection tubes were monitored with a commercial ultraviolet absorption recording machine. Ultraviolet absorption analysis at 280 m$\mu$ were made of the contents of the tubes and those belonging to an absorption peak were pooled and designated by pooled fraction number. Representative samples were employed for chloride ion analysis and portions of representative samples were dialyzed against physiological phosphate buffer systems. Dialyzed samples were filtered through a sterile filtration membrane (0.20 micron pore size).

A feline tongue cell suspension containing 130,000 viable cells per milliliter was prepared from frozen cells of an established cell line in the nutrient cell growth medium previously described. To separate 4.5 milliliter portions of this cell suspension were added 0.5 milliliter portions of (a) non-adsorbed, undialyzed serum with pH adjusted to physiological as control (b) undialyzed serum after adsorption and (c) dialyzed samples of serum fractions to produce cell suspension samples containing 10 percent (volume/volume) final concentrations of one of the test samples. The resulting samples were mixed well and 2 milliliter portions were seeded into wells of multi-dish culture trays and incubated at 37° C. in 5 percent carbon dioxide and 100 percent humidity atmosphere for two days. The readings taken at the end of this period showed that the sample containing medium with pooled No. 2 fraction promoted high growth, smooth, normal looking cells of about 75 percent confluency. The appearance and the confluency were similar to that of serum control. The fractions designated No. 3 and No. 4 promoted cell growth to a lesser degree with about 50 percent or lesser confluency. Chloride ion analyses of several representative fractions and tubes indicated that the active materials had been eluted with 0.05 M sodium phosphate buffer of pH 7.2 having a chloride ion concentration between 0.05 M and 1.60 M.

EXAMPLE III

In a similar operation, to 5050 milliliters of pooled adult and fetal bovine serum of initial pH of 7.58 was added 17.2 milliliters of 10 N sodium hydroxide to adjust the serum pH to 10.5. A 50 milliliter sample of the pH adjusted serum was taken as serum control. To the remaining serum, 60.0 grams of QAE-Sephadex A-50 anion exchanger was added and the mixture stirred for about 17 hours at 4° C. The resulting exchanger gel was filtered and washed several times with 0.05 M sodium phosphate buffer of pH 7.2 containing 0.05 M sodium chloride, allowed to stand overnight in about 10 liters of the same concentration buffer-sodium chloride solution, washed with fresh buffer-salt solution, placed in a column (5 centimeters diameter; height of gel 54 centimeters) and washed again with the buffered salt solution. Thereafter, a 1.60 M sodium chloride - 0.05 M sodium phosphate solution of pH 7.2 was applied to the column to elute the growth promoting material. Fifteen milliliter fractions were collected. Portions of the collected material were pooled as before and samples of the fractions were dialyzed and sterile filtered.

Activity in promoting cell growth was determined employing feline tongue and canine kidney cell cultures in the manner similar to that previously described and observations made with feline tongue after 2 days and with canine kidney after four days. The results of the eluted fractions and comparison with serum is seen in Table II.

TABLE II

| Culture Sample | Concentration (percent) | OBSERVATIONS | |
|---|---|---|---|
| | | Feline Tongue | Canine Kidney |
| Serum Control | 10 | 100% confluent, smooth cell sheet | 50-75 confluent, smooth cells |
| Serum after adsorption | " | ≦Few attached cells; all rounded up | Many attached, rounded up cells |
| End of wash | " | >50% confluent, smooth cells* | ≈75% confluent, uniform smooth cells |
| No. 1 Pooled Fraction | " | >50% confluent | Many attached, rounded up |

TABLE II-continued

| Culture Sample | Concentration (percent) | OBSERVATIONS Feline Tongue | Canine Kidney |
|---|---|---|---|
| No. 2 Pooled Fraction | " | <75% confluent smooth cells | cells, no outgrowth Many attached, rounded up cells, no outgrowth |
| No. 3 Pooled Fraction | " | 100% confluent very dense cell sheet | ≈25% confluent, smooth, uniform cell sheet** |
| No. 3 Pooled Fraction | 5 | 100% confluent very dense cell sheet | — |
| No. 3 Pooled Fraction | 2 | 100% confluent very dense cell sheet | 75-90% confluent, smooth, uniform cell sheet** |
| No. 3 Pooled Fraction | 1 | 100% confluent very dense cell sheet | 100% confluent, smooth, uniform cell sheet** |
| No. 3 Pooled Fraction | 0.5 | — | 100% confluent, smooth, uniform cell sheet** |

*The wash contained some sodium chloride; activity probably due to leaching out of growth material during washing step.
**Probable cause of poor growth is possible high ionic strength to which canine kidney cells are more sensitive than feline tongue cells.

The effect on growth of different concentrations were also studied employing pooled Fraction No. 3. In repeated tests with canine kidney cells, the results of three day old cultures were as follows:

| Sample | | | Observation* |
|---|---|---|---|
| 10% | Serum Control | 50-75% | confluent, good smooth cells |
| 2% | Serum Control | 50-75% | confluent, good smooth cells |
| 1% | Serum Control | 50-75% | confluent, good smooth cells |
| 0.5% | Serum Control | ≈75% | confluent, good smooth cells |
| 0.2% | Serum Control | 75-90% | confluent, good smooth cells |
| 0.1% | Serum Control | ≈50% | confluent, good smooth cells |
| 10% | Pooled Fraction #3 | <50% | confluent, good smooth cells |
| 2% | Pooled Fraction #3 | ≈75% | confluent, good smooth cells |
| 1% | Pooled Fraction #3 | 100% | confluent, good smooth cells |
| 0.5% | Pooled Fraction #3 | 100% | confluent, good smooth cells |
| 0.2% | Pooled Fraction #3 | 100% | confluent, good smooth cells |
| 0.1% | Pooled Fraction #3 | 100% | confluent, good smooth cells |

*Probable cause of poorer cell growth of both serum control and pooled fraction at higher concentrations is possible high ionic strength.

Pooled Fraction No. 3 superior to serum control in promoting the growth of feline tongue and canine kidney cells in these tests.

What is claimed is:

1. A composition comprising material suitable for promoting cell growth, said material prepared by a method which comprises
   (1) contacting serum at a pH in the range of about 8 to 11 with an anion exchanger while the temperature is maintained below about 5° C. to adsorb growth-promoting material thereon, and
   (2) eluting said growth-promoting material from the anion exchanger with a gradient salt solution in the pH range of 7.0 to 7.6 or with a gradient pH solution in the range of 10.5 to 4, said elution being carried out after first washing the exchanger until the wash solution shows a low and substantially constant optical density at 280 mμ.

2. A composition according to claim 1 in which the method employs an anion exchanger which is a carbohydrate backboned anion exchanger for the adsorption step.

3. A composition according to claim 2 in which the anion exchanger is a dextran backboned anion exchanger.

4. A composition according to claim 1 in which the method employs a gradient salt solution for the elution step.

5. A composition according to claim 4 in which the gradient salt solution is in a physiological buffer system.

6. A composition according to claim 1 in which the serum is bovine serum.

7. A composition suitable for promoting cell growth which comprises a product prepared from serum by
   (1) adding sodium hydroxide solution to serum at temperatures maintained in the range of about 1° to 6° C. and mixing until the pH of the serum is in the range of about 9.5 to 10.5,
   (2) adding to the resulting alkaline serum a carbohydrate based anion exchanger and mixing for a period of from about 16 to 24 hours while the temperature is maintained below about 5° C. to adsorb growth promoting material on the exchanger,
   (3) mechanically separating the resulting exchanger from the liquid,
   (4) washing the exchanger with 0.05 M sodium phosphate buffer solution of pH in the range of 7.0 to 7.6 until the wash solution shows a substantially constant optical density at 280 mμ,
   (5) eluting with gradient sodium chloride solution in the concentration range of about 0.2 to about 2.0 M, and
   (6) recovering the eluate.

8. A process for preparing a purified growth promoting material from serum which comprises
   (1) contacting serum at a pH in the range of about 8 to 11 with an anion exchanger while the temperature is maintained below about 5° C. to adsorb growth promoting material thereon, and
   (2) eluting said growth-promoting material from the anion exchanger with a gradient salt solution in the pH range of 7.0 to 7.6 or with a gradient pH solution in the range of 10.5 to 4, said elution being carried out after first washing the exchanger until the wash solution shows a low and substantially constant optical density at 280 mμ.

9. A process according to claim 8 in which a gradient salt solution is employed for eluting.

10. A process according to claim 9 in which the gradient salt solution is in a physiological buffer system.

11. A process for preparing a purified growth promoting material from serum which comprises
   (1) adding sodium hydroxide solution to serum at temperatures maintained in the range of about 1° to 6° C. and mixing until the pH of the serum is in the range of about 8 to 11,
   (2) adding to the resulting alkaline serum an carbohydrate based anion exchanger and mixing for a period of from about 16 to 24 hours while the temperature is maintained below about 5° C. to adsorb growth promoting material on the exchanger,
   (3) mechanically separating the resulting exchanger from the liquid,
   (4) washing the exchanger with 0.05 M sodium phosphate buffer solution of pH in the range of 7.0 to 7.6 until the wash solution shows a substantially constant optical density at 280 m$\mu$,
   (5) eluting with gradient sodium chloride solution in the concentration range of about 0.2 M to about 2.0 M, and
   (6) recovering the eluate.

* * * * *